United States Patent [19] [11] 4,405,812
Dean et al. [45] Sep. 20, 1983

[54] PROCESS FOR ORTHO DEALKYLATION OF AROMATIC AMINES

[75] Inventors: Walter K. Dean, Huntington Woods; Bernard R. Meltsner, Royal Oak, both of Mich.

[73] Assignee: Ethyl Corporation, Richmond, Va.

[21] Appl. No.: 350,204

[22] Filed: Feb. 19, 1982

[51] Int. Cl.$^3$ .................. C07C 85/24; C07C 85/20
[52] U.S. Cl. ................................ 564/409; 564/486
[58] Field of Search ............................ 564/409, 416

[56] References Cited

U.S. PATENT DOCUMENTS

| | | | |
|---|---|---|---|
| 2,377,071 | 5/1945 | Castner et al. | 564/416 |
| 3,293,295 | 12/1966 | Swakon et al. | 564/416 |
| 3,504,035 | 3/1970 | Polinski et al. | 564/416 |
| 4,198,350 | 4/1980 | Fields | 564/409 X |
| 4,317,931 | 3/1982 | Wollensak et al. | 564/409 |

FOREIGN PATENT DOCUMENTS

| | | | |
|---|---|---|---|
| 49-29177 | 8/1974 | Japan | 564/409 |
| 49-29178 | 8/1974 | Japan | 564/409 |

OTHER PUBLICATIONS

Janzen, "Journal of the American Chemical Society", vol. 87:15, pp. 3531 & 3532 (1965).
Fields et al., "Journal of the American Chemical Society", vol. 89:13, pp. 3224–3228 (1967).

Primary Examiner—John Doll
Attorney, Agent, or Firm—Donald L. Johnson; John F. Sieberth; Joseph D. Odenweller

[57] ABSTRACT

Ortho-methyl groups are preferentially removed from o-methyl substituted aromatic amines by contacting with a nickel catalyst at about 200°–400° C.

5 Claims, No Drawings

PROCESS FOR ORTHO DEALKYLATION OF AROMATIC AMINES

BACKGROUND

Aromatic amines such as aniline are made commercially by nitrating the aromatic ring and reducing the nitro group to an amine group. Alkyl substituted aromatic amines are made in the same manner by nitrating the alkyl aromatic followed by reduction. Alkyl substituents are ortho-para directing so this process is not well suited to making meta-alkyl aromatic amines.

Many of the products made by the process have known utility. Meta-toluidine is used to make dyes. Aniline is also useful in making dyes. It can be readily converted to N-methyl aniline, an organic antiknock agent in gasoline.

SUMMARY OF THE INVENTION

It has now been discovered that alkyl substituted aromatic amines can be dealkylated by contacting a nickel catalyst at elevated temperatures. Ortho-alkyl groups are preferentially removed.

DESCRIPTION OF PREFERRED EMBODIMENTS

A preferred embodiment of the invention is a process for selectively removing an ortho-methyl substituent from an aromatic amine having at least one nuclear methyl substituent ortho to an amine group, said process comprising contacting said aromatic amine with a nickel catalyst at an elevated temperature of about 200°-400° C.

The process can be used to remove an ortho-methyl group from a broad range of aromatic amines having an ortho-methyl substituent. Representative examples include ortho-toluidine, 2,6-dimethyl aniline, 2,4-dimethyl aniline, 2,4,6-trimethyl aniline, 2-methyl-4-chloro aniline, 2-methyl-α-naphthyl amine, 2,5-dimethyl aniline, 2-methyl-4-tert-butylaniline, 2-methyl-5-bromo aniline, 2-methyl-3-aminophenathrene, 2-methyl-α-aminoanthracene, and the like.

The process is most applicable to ortho-methyl substituted anilines such as ortho-toluidine, 2,4-dimethyl aniline, 2,5-dimethyl aniline, 2,4,6-trimethyl aniline, and the like.

The process should be conducted at a temperature high enough to cause the desired demethylation but not so high as to cause undesired decomposition. A useful temperature range in which to experiment is about 200°-500° C. A more preferred temperature range is about 200°-400° C. A most preferred range is about 300°-375° C.

The catalyst can be either nickel metal or nickel on a suitable support. Other metals may be present as long as they do not interfere with the catalytic effect of nickel. In supported nickel catalysts, the nickel content can vary from 1 to about 70 weight percent. A preferred supported catalyst contains about 50 weight percent nickel. Suitable supports include silica, alumina, silica alumina, Kieselguhr, zirconia, magnesia, and the like.

The process can be carried out on a continuous basis by placing the catalyst in a heated tube and passing the aromatic amine through the heated catalyst bed. If desired, the aromatic amine can be initially vaporized and the vapor passed through the heated catalyst. Alternatively, the aromatic amine can be fed to the catalyst bed in a liquid phase. Whether it remains liquid or is vaporized will then depend upon the temperature of the catalyst bed and the boiling point of the aromatic amine. In many cases the reactant in the catalyst bed is a mixed vapor-liquid phase.

Average contact time between the aromatic amine and the catalyst can vary over a wide range. Optimum contact time can be readily determined by a few experiments. A useful range is from a few seconds to several hours and a preferred contact time is about 5 seconds to 60 minutes.

After the catalytic reaction, the product mixture is cooled and can be separated into components by distillation.

Initially it has been observed that both demethylation and deamination of the aromatic amine occur. After operating for a few hours, deamination decreases and ortho demethylation becomes the main reaction.

The following examples show how the process can be conducted.

EXAMPLE 1

The catalyst used was a 50 weight percent nickel supported on Kieselguhr (Harshaw Ni-0105T 3/16"). A 14 gram portion of this catalyst was placed in a stainless steel tube 6" by ½" diameter. The catalyst tube was electrically heated to 315° C. and a solution of 8 ml. 2,4-dimethyl aniline in 40 ml. benzene was fed at the top of the tube over a six hour 50 minute period. Temperature of the tube was held in the range of 346°-360° C. Effluent leaving the bottom of the tube was cooled. A sample of the effluent at the 5 hour 40 minute point was analyzed by gas chromatography. Excluding the benzene solvent, the major identified components on a normalized basis were:

|  | Area Percent |
|---|---|
| Toluene | 29.7 |
| Aniline | 0.18 |
| ortho-Toluidine | 2.4 |
| para-Toluidine | 9.5 |
| 2,4-Dimethyl aniline | 51.0 |
| 2,6-Dimethyl aniline | 0.7 |
| 2,4,6-Trimethyl aniline | 1.3 |

Of the mono-demethylated products (viz, toluidine) there is 3.96 times as much para-toluidine as there is ortho-toluidine showing that the process selectively preferred ortho-demethylation.

EXAMPLE 2

The above procedure was repeated using as feed stock a solution of 8 ml. ortho-toluidine in 40 ml benzene. The identified components in the effluent on a normalized basis excluding benzene were as follows:

|  | Area Percent |
|---|---|
| Toluene | 15.4 |
| Aniline | 22.6 |
| Ortho-Toluidine | 51.4 |
| N—Methyl-m-toluidine | 0.3 |
| 2,6-Dimethyl aniline | 0.7 |
| 2,4-Dimethyl aniline | 0.4 |
| 2,4,6-Trimethyl aniline | 0.5 |

EXAMPLE 3

This experiment used the same tubular reactor and catalyst as in Example 1. The feed stock was 16 ml. of 2,5-dimethyl aniline without any solvent. The catalyst tube was held at 352°–355° C. and feed time was about seven hours. Samples of the effluent product were taken periodically and analyzed by gas chromatography. Results were as follows:

| Time on Stream, min. | 45 | 105 | 165 | 225 | 285 | 345 | 405 |
|---|---|---|---|---|---|---|---|
| Conversion (%)[1] | 98.8 | 92.2 | 70.1 | 53.8 | 44.4 | 38.1 | 33.3 |
| Selectivity to: (%)[2] | | | | | | | |
| Benzene | 32.7 | 11.3 | 7.8 | 6.7 | 6.1 | 5.2 | 5.4 |
| Toluene | 62.4 | 71.6 | 52.4 | 44.6 | 40.3 | 37.0 | 37.5 |
| p-Xylene | 2.8 | 3.6 | 2.9 | 2.8 | 2.9 | 2.9 | 3.3 |
| o-Xylene | 1.2 | 2.5 | 2.4 | 2.2 | 2.0 | 1.8 | 1.8 |
| Aniline | 0.1 | 1.3 | 2.4 | 2.0 | 2.0 | 1.8 | 1.8 |
| Toluidines[3] | 0.5 | 8.9 | 29.1 | 37.7 | 40.8 | 43.8 | 46.8 |
| Heavy Ends | 0 | 0.5 | 2.6 | 3.5 | 5.4 | 7.6 | 9.0 |

[1] GC area percent
[2] GC area percent, as percent of total products
[3] 95 percent meta isomer by capillary GC

EXAMPLE 4

This example used the same equipment as used in Example 1, except that the catalyst was 14.2 grams of supported nickel catalyst (Harshaw Ni0105T). Feed stock was 27 ml. of 2,5-dimethyl aniline. Feed was started at 375° C. and continued at 347°–359° C. for 8 hours during which time 16.5 ml. was fed to the packed column. The reaction was shut down overnight and resumed the next morning. Feed was continued at 345°–369° C. for 8 hours 25 minutes. The total feed was 27 ml. of 2,5-dimethyl aniline. Samples of the effluent were taken periodically and analyzed by gas chromatography. The results in area percent were as follows:

| | Hours from Start | | | | |
|---|---|---|---|---|---|
| | 1 | 4 | 8 | 12 | 16 |
| Benzene | 36 | 7 | 3 | 4 | 4 |
| Toluene | 54 | 54 | 25 | 28 | 28 |
| Xylenes | 3 | 6 | 4 | 4 | 5 |
| Aniline | 0.1 | 2 | 1 | 1 | 1 |
| m-Toluidine | 1 | 14 | 19 | 19 | 18 |
| 2,5-DMA | 5 | 17 | 46 | 38 | 38 |

EXAMPLE 5

This run was carried out in the same equipment as used in Example 1. The catalyst was 14.0 grams of silica supported nickel (54 percent weight Ni). Feed stock was a solution of 4.9 grams of 2,5-di-tert-butyl aniline in 45.5 ml. of benzene. Feed time was 8 hours and the catalyst was held at 223°–232° C. during the first 5 hours and then lowered to 198°–205° C. for the remaining feed time. Samples of the effluent were taken periodically and analyzed by gas chromatography with the following results in area percent.

| | Hours from Start | | | | |
|---|---|---|---|---|---|
| | 1 | 2 | 4 | 6 | 8 |
| Isobutylene | 0.4 | 1.3 | 2.7 | 1.9 | 1.5 |
| Benzene | 97.8 | 97.9 | 96.4 | 92 | 93 |
| Tert-butyl benzene | 0.3 | 0.3 | 0.1 | 0.2 | |
| m-Tert-butyl aniline | — | — | 0.8 | 5.8 | 5.0 |

-continued

| | Hours from Start | | | | |
|---|---|---|---|---|---|
| | 1 | 2 | 4 | 6 | 8 |
| 2,5-Di-tert-butyl aniline | — | — | — | — | 0.04 |

These results show that the tert-alkyl groups are almost completely removed, especially at high temperatures but indicates that even with tert-alkyl groups the process prefers removal of ortho groups.

A highly preferred embodiment of the invention is a process for making m-toluidine from p-xylene. In this embodiment, p-xylene is mono-nitrated by any of several well-known procedures such as by slowly adding p-xylene to concentrated nitric acid or mixed concentrated nitric and sulfuric acids. The major product of the nitration is 2,5-dimethyl nitrobenzene. This compound is easily reduced to 2,5-dimethyl aniline by standard reducing methods such as by adding iron chips and 30 percent aqueous HCl to the 2,5-dimethyl nitrobenzene. Alternatively, it can be reduced with a mixture of granular zinc and aqueous sodium hydroxide. Another method is by catalytic hydrogenation over a catalyst such as Raney nickel. If desired, the 2,5-dimethyl aniline can be purified at this time by distillation although the crude product can be used as feed stock to the final step.

In the final step, the 2,5-dimethyl aniline is contacted with a nickel catalyst at 200°–400° C., more preferably 300°–375° C., to selectively remove the o-methyl group leaving a product mixture containing a substantial amount of m-toluidine which can be recovered by distillation.

We claim:

1. A process for selectively removing an ortho-methyl substituent from an aromatic amine having at least one nuclear methyl substituent ortho to an amine group, said process comprising contacting said aromatic amine with a nickel catalyst at an elevated temperature of about 200°–400° C.

2. A process of claim 2 wherein said aromatic amine is an o-methyl substituted aniline.

3. A process of claim 2 wherein said aniline is 2,5-dimethyl aniline.

4. A process of claim 2 for making m-toluidine, said process comprising contacting 2,5-dimethyl aniline with a nickel catalyst at an elevated temperature of about 300°–375° C. whereby the 2-methyl group is preferentially removed forming m-toluidine.

5. A process for making m-toluidine, said process comprising (a) nitrating p-xylene to form 2,5-dimethyl nitrobenzene, (b) reducing said 2,5-dimethylnitrobenzene to form 2,5-dimethyl aniline, (c) contacting said 2,5-dimethyl aniline with a nickel catalyst at an elevated temperature of about 200°–400° C. to selectively remove the o-methyl group and (d) recovering m-toluidine from the reaction product.

* * * * *